(12) United States Patent
Stoutamire

(10) Patent No.: US 8,153,688 B2
(45) Date of Patent: *Apr. 10, 2012

(54) ESTERS OF 2-PHENYLALKANENITRILES AND ANTIFUNGAL COMPOSITIONS CONTAINING THEM

(75) Inventor: Donald Wesley Stoutamire, Modesto, CA (US)

(73) Assignee: MCS Laboratories, Inc., Modesto, CA (US)

( * ) Notice: Subject to any disclaimer, the term of this patent is extended or adjusted under 35 U.S.C. 154(b) by 317 days.

This patent is subject to a terminal disclaimer.

(21) Appl. No.: 12/448,192

(22) PCT Filed: Dec. 10, 2007

(86) PCT No.: PCT/US2007/025352
§ 371 (c)(1), (2), (4) Date: Jun. 12, 2009

(87) PCT Pub. No.: WO2008/088538
PCT Pub. Date: Jul. 24, 2008

(65) Prior Publication Data
US 2010/0022640 A1    Jan. 28, 2010

(51) Int. Cl.
*A61K 31/275*  (2006.01)
*A61K 31/215*  (2006.01)
*C07C 255/03*  (2006.01)
*C07C 229/00*  (2006.01)

(52) U.S. Cl. ........... 514/520; 514/529; 558/388; 560/38

(58) Field of Classification Search .................. 514/520, 514/529; 558/388; 560/38
See application file for complete search history.

(56) References Cited

U.S. PATENT DOCUMENTS

| 3,485,925 A | 12/1969 | Page |
| 3,513,186 A | 5/1970 | Kudema, Jr. |
| 4,267,179 A | 5/1981 | Heeres et al. |
| 4,709,078 A | 11/1987 | Schirmer et al. |
| 4,782,177 A | 11/1988 | Schirmer et al. |
| 7,622,504 B2 * | 11/2009 | Stoutamire .................. 514/529 |

OTHER PUBLICATIONS

Fedorynski et al. CAS Accession No. 1977:154699.*
Reynaud et al. CAS Accession No. 1952:45245.*
Dai Sig Im, Chan Seong Cheong, Ha Lee, Lipase-catalyzed remote kinetic resolution of nitriles . . . etc. Jounal of Molecular Catalysis B: Enzymatic 26 (2003) 131-143.
Michal Fedorynski et al, Reactions of Organic Anions LXXI. Reactions of Enol Ethers . . . etc.,Inst. Organic Chem. and Technology, Technical Univ., Warsaw, Kosykowa 75 Poland, Synthesis, 1977, p. 120-122.

* cited by examiner

*Primary Examiner* — Joseph Kosack
(74) *Attorney, Agent, or Firm* — Leonard P. Miller

(57) ABSTRACT

Esters of 2-phenylalkanenitriles, such as 3-acetoxy-2-(2-chloro-5-(difluoromethoxy)phenyl)propanenitrile and 3-acetoxy-2-(4-chlorophenyl)propanenitrile, and compositions containing such esters, are useful as fungicides at very low concentrations.

14 Claims, No Drawings

ESTERS OF 2-PHENYLALKANENITRILES AND ANTIFUNGAL COMPOSITIONS CONTAINING THEM

BACKGROUND OF THE INVENTION

1. Field of the Invention

This invention relates to a novel class of esters of 2-phenylalkanenitriles and to antifungal compositions containing such esters.

2. Description of the Related Art

There are a number of chemical compounds disclosed in the art which are said to have antifungal and/or antibacterial activity. For example, U.S. Pat. No. 4,267,179 describes certain heterocyclic derivatives of (4-phenylpiperazine-1-yl-aryloxymethyl-1,3-dioxolan-2-yl)-1H-imidazoles and 1H-1,2,4-triazoles which are taught to be useful as antifungal and antibacterial agents. U.S. Pat. No. 4,709,078 discloses certain acrylates, such as methyl α-(2-benzyloxy phenyl)-β-methoxyacrylate, and certain fungicidal compositions containing such acrylate compounds. U.S. Pat. No. 3,485,925 describes certain ortho-haloatroponitriles which are said to be useful in inhibiting the growth of microorganisms. The novel compounds of the present invention differ from the prior art compounds in that they are not imidazoles, triazoles, acrylates or atroponitriles, but instead are esters of substituted phenylalkanenitriles, which have been found to be highly effective antifungal agents even at relatively low concentrations.

The syntheses of various synthetic intermediates, including certain esters of substituted phenylalkanenitriles, derived from tertiary arylic alcohols are disclosed in the article: "Lipase-catalyzed remote kinetic resolution of arylic nitrites with adjacent quaternary chiral center and the determination of their absolute configuration", Dai Sig Im, Chan Seong Cheong, So Ha Lee, Journal of Molecular Catalysis B: Enzymatic 26 (2003) 131-143. The ester compounds disclosed in this article are not disclosed to have antifungal or antibacterial activity, and differ structurally from the esters of the present invention in that they are substituted in the alpha position to the nitrile group. It is an important feature of the esters of the present invention that the alpha position to the nitrile group not be substituted.

SUMMARY OF THE INVENTION

This invention concerns certain novel esters of 2-phenylalkanenitriles and to antifungal compositions containing such esters. These ester compounds and compositions containing them, have been found to have outstanding antifungal properties. The compounds of the invention can be described by the formula:

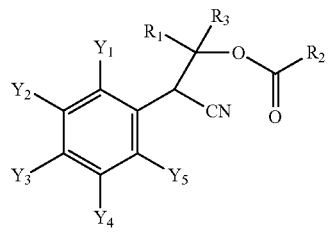

wherein $R_1$ is hydrogen, $C_1$-$C_5$ alkyl, $C_1$-$C_5$ alkoxyalkyl, or $C_1$-$C_5$ alkoxycarbonyl, $R_2$ is hydrogen, $C_1$-$C_5$ alkyl, phenyl or $CH_2$-phenyl, $R_3$ is hydrogen, $C_1$-$C_5$ alkyl, or substituted phenyl, and $Y_1, Y_2, Y_3, Y_4$ and $Y_5$ are individually or collectively hydrogen, halogen, methyl, —$CHF_2$, —$CF_3$, —$OCHF_2$, —$OCF_3$, $C_1$-$C_5$ alkoxy, phenoxy, or —$SF_5$, with the proviso that at least two of $Y_1, Y_2, Y_3, Y_4$ and $Y_5$ must be hydrogen.

As can be seen from the foregoing formula, the compounds of the invention include esters of 2-phenylalkanenitriles wherein the remainder of the positions on the phenyl ring are not substituted, wherein the phenyl ring has one substituent in addition to the alkanenitrile substituent (mono ring-substituted esters), wherein the phenyl ring has two substituents in addition to the alkanenitrile substituent (ring-disubstituted esters) and wherein the phenyl ring has three substituents in addition to the alkanenitrile substituent (ring-trisubstituted esters).

Typical esters of the invention without additional substituents on the phenyl ring include 3-acetoxy-2-phenylpropanenitrile, 3-(formyloxy)-2-phenylpropanenitrile and 3-acetoxy-2-phenylbutanenitrile.

Typical mono ring-substituted esters of the invention include 3-acetoxy-2-(2-chlorophenyl)propanenitrile, 3-acetoxy-2-2-bromophenyl)propanenitrile, 3-acetoxy-2-(2-(difluoromethyl)phenyl)propanenitrile, 2-(2-chlorophenyl)-3-(formyloxy)propanenitrile, 3-acetoxy-2-(2-(difluoromethoxy)phenyl)propanenitrile, 3-acetoxy-2-(2-(trifluoromethoxy)phenyl)propanenitrile, 3-acetoxy-2-(2-(trifluoromethyl)phenyl)propanenitrile, 3-acetoxy-2-3-phenoxyphenyl)propanenitrile, 3-acetoxy-2-4-chlorophenyl)butanenitrile, 3-acetoxy-2-(4-chlorophenyl)-3-methylbutanenitrile and the like.

Representative ring-disubstituted esters of the invention include 2-(2,5-dichlorophenyl)-3-(formyloxy)propanenitrile, 3-acetoxy-2-(2,4-dichlorophenyl)propanenitrile, 3-acetoxy-2-(2,5-bis(difluoromethoxy)phenyl)propanenitrile, 3-acetoxy-2-(5-chloro-2-(difluoromethoxy)phenyl)propanenitrile, 3-acetoxy-2-(2-chloro-5-(trifluoromethyl)phenyl)propanenitrile, 2-(2-chloro-5-(difluoromethoxy)phenyl)-3-(formyloxy)propanenitrile, 3-acetoxy-2-(2-chloro-5-(difluoromethoxy)phenyl)propanenitrile, 3-acetoxy-2-(5-chloro-2-(difluoromethoxy)phenyl)propanenitrile, 2-(2,4-dichlorophenyl)-3-(phenylacetoxy)propanenitrile, 2-(2-chloro-5-difluoromethoxy)phenyl)-3-(phenylacetoxy)propanenitrile, 3-acetoxy-2-(2,5-dichlorophenyl)propanenitrile and the like.

Typical tri ring-substituted esters of the invention include 3-acetoxy-2-(2,3,4-trichlorophenyl)propanenitrile, 3-acetoxy-2-(2,3,5-trifluorophenyl)propanenitrile, 3-acetoxy-2-(2,4,6-tribromophenyl)propanenitrile and the like.

DESCRIPTION OF PREFERRED EMBODIMENTS

This invention is concerned with esters of 2-phenylalkanenitriles as described by the above formula, wherein the ester group may be variously formate (formyloxy), acetate (acetoxy), propionate, butyrate, valerate, caproate, benzoate (phenylformyloxy) or phenylacetate (phenylacetoxy), depending on whether $R_2$ in the above formula is hydrogen, $C_1$ (methyl), $C_2$ (ethyl), $C_3$ (Propyl), $C_4$ (butyl), $C_5$ (pentyl), phenyl or $CH_2$-phenyl. Of the foregoing esters, compounds based on the formate ester ($R_2$=hydrogen) and the acetate ester ($R_2$=$C_1$) are preferred, with compounds based on the acetate ester being the most preferred.

The esters of the invention include compounds wherein $R_1$ in the above formula is hydrogen, $C_1$-$C_5$ alkyl, or $C_1$-$C_5$ alkoxyalkyl and $R_3$ in the above formula is hydrogen, $C_1$-$C_5$ alkyl or substituted phenyl. In cases where $R_3$ is a substituted phenyl, a negatively substituted phenyl group is preferred such as chlorophenyl, difluoromethoxyphenyl, trifluoromethylphenyl and the like. Preferred ester compounds include those wherein $R_1$ is hydrogen, methyl, methoxy methyl, or ethoxy carbonyl, and $R_3$ is hydrogen or methyl, with ester compounds wherein $R_1$ is hydrogen and $R_3$ is hydrogen or methyl being most preferred.

When $Y_1$, $Y_2$, $Y_3$, $Y_4$ and $Y_5$ in the above formula are halogens, they may be selected from any of the halogens, e.g., fluorine, chlorine, bromine, or iodine. However, the most active halogen-substituted esters are those wherein $Y_1$, $Y_2$, $Y_3$, and $Y_4$ in the above formula represent one or more middle halogens, i.e., chlorine or bromine. Accordingly, a preferred class of ester compounds of this invention is that wherein one or more of $Y_1$, $Y_2$, $Y_3$, $Y_4$ and $Y_5$ substituents on the phenyl ring are middle halogens. Particularly preferred are ester compounds wherein $Y_1$ is chlorine, $Y_3$ is chlorine or where $Y_1$ and $Y_4$ are chlorine. Another preferred class of esters of this invention are those having one or more —OCHF$_2$ (difluoromethoxy) substituents on the phenyl ring. A further preferred class of esters of this invention is that having a middle halogen substituent (such as chlorine) on the phenyl ring in combination with a difluoromethoxy substituent (e.g., ester compounds wherein $Y_1$ is chlorine while $Y_4$ is difluoromethoxy).

Preparation

The esters of the present invention may be prepared from the corresponding substituted phenylacetonitriles. Reaction of a 2-substituted arylacetonitrile with formaldehyde in the presence of a catalytic amount of base gives the 2-hydroxymethyl derivative. Suitable catalytic bases include DBN (1,5-diazobiclclo[4.3.0 non-5-ene]), DBU (1,8-diazobicyclo [5.4.0-undec-7-ene]), Triton B® (benzyltrimethylammonium hydroxide) and the like, as well as inorganic bases such as the alkali metal hydroxides. The alcohol function is then acylated by an acid catalyzed reaction with an appropriate acid anhydride. Suitable acid catalysts include sulfuric acid, hydrogen chloride, boron trifluoride and the like. Formylation of the hydroxyl function is also readily accomplished by reaction with the Vilsmeier reagent prepared from dimethylformamide. Alpha hydroxymethylation of phenylacetonitriles can also be accomplished by initial condensation with diethyl oxalate followed by treatment with formaldehyde and a base as described in the literature. [T. N. Robinson, A. J. Cross, A. R. Green, J. M. Toczek, and B. R. Boar, British Journal of Pharmacology (1989), 98, 833-840.] The alpha-hydroxy intermediates may also be prepared by acylation of the substituted phenylacetonitriles by esters such as ethyl formate, ethyl acetate, ethyl methoxyacetate, ethyl phenylacetate, and the like to give 3-oxonitriles which can be reduced to the intermediate alcohols. The esters of the present invention may also be prepared by acylation of the above 3-oxonitriles with acylating agents such as acid anhydrides followed by reduction of the resulting unsaturated esters.

The esters of the present invention may be used to inhibit the growth of a broad spectrum of microorganisms including bacteria and fungi. The esters of the invention are particularly effective against the fungi, e.g. yeasts and molds, including human-pathogenic fungi, such as *Trichophyton metagrophytes* and *Canida albicans*. In addition to having a high degree of effectiveness against a wide variety of pathogenic and nonpathogenic microorganisms, the esters of the present invention are believed to have the added advantage of being relatively non-toxic to mammals. Thus, the present esters are potentially useful in a wide range of applications, including use as a microbiocide in and on warm-blooded animals, including humans. Potential therapeutic uses include the treatment of dermaphtyic diseases such as ring worm and athlete's foot, as well as fungal infection of the toenails (onychomycosis).

The esters of the invention may be applied as is, but more typically are used in combination with one or more other ingredients such as liquid or solid carriers and surfactants. The ester compositions of the invention can be prepared as a concentrate or as a ready to use formulation. Such compositions can be prepared and/or used in the form of a solution, emulsion, paste, gel, suspension, powder, dust, or granules. Suitable liquid carriers include neutral hydrocarbons such as kerosene and mineral oil distillates, and natural and synthetic oils and organic solvents. Suitable solid carriers include neutral materials such as talc, diatomaceous earth and the like, and polymers such as PVC, styrene and polypropylene and the like. Suitable surface active agents include non-ionic surfactants and phenol-ethylene oxide condensates and the like.

The concentration of the esters of the invention necessary for inhibiting the growth of fungi and bacteria will vary depending on the particular species of ester, the type of fungi or bacteria, whether or not a carrier is included, and environmental conditions, etc. Those skilled in the art can readily determine a suitable concentration for a particular application. When the esters of the invention are admixed with a carrier, the amount of ester in the composition will generally range from about 0.001 percent to 95 percent by weight of the total composition, preferably from 0.01 percent to 10 percent by weight, of the total composition. Because of their exceptional activity, in many applications the concentration of the ester in the compositions of the invention will be relatively low, e.g., from about 0.01 percent to 1 percent by weight.

EXAMPLES

The following examples are provided for purposes of illustrating the present invention, and are not intended in any way to be limiting.

Example 1

Preparation of 2-chloro-5-(difluoromethoxy)toluene

A 100 milliliter (mL) 3-neck flask fitted with a magnetic stir bar, thermometer and gas inlet tube with an attached rubber balloon was charged with a solution of 9 grams (g) (0.16 M) of KOH in 15 mL of water, 10 g (0.0701 M) of 4-chloro-3-methylphenol, and 150 milligrams (mg) of tetrabutylammonium sulfate and 10 mL of tetrahydrofuran (THF). The reaction flask was flushed with chlorodifluoromethane (Freon) and the mixture was stirred vigorously and cooled to 30-40° C. while keeping the balloon partially inflated with Freon. When the reaction slowed after 1.5 hours, an additional 4 g of KOH was added. When the reaction again slowed, the mixture was diluted with water and extracted with hexane. The organic phase was washed with 2 N KOH solution, dried (Na$_2$SO$_4$), stripped, and the residue was distilled through a short path head to collect 8.9 g (66%), b.p. 60-65° C. (~5 torr.) of 2-chloro-5-(difluoromethoxy)toluene as a colorless liquid.

Similarly produced was: 5-chloro-2-(difluoromethoxy) toluene in 58% yield.

Example 2

Preparation of 2-bromomethyl-1-chloro-4-difluoromethoxy)benzene

A 50 mL 3-neck flask fitted with a magnetic stir bar, thermometer and a reflux condenser was charged with 4.25 g (22.1 mmol) of 2-chloro-5-(difluoromethoxy)toluene, 17 mL of carbon tetrachloride (CCl$_4$), 4.12 g (23.2 mmol) of N-bromosuccinimide and 65 mg of benzoyl peroxide. After 4 hours of reflux, the mixture became light yellow and all solids were less dense than the solvent. The mixture was filtered to remove succinimide and most of the CCl$_4$ was distilled off through a short column to a pot temperature of 110° C. The residue was chromatographed on 75 g of silica gel and mixed fractions were rechromatographed to separate 1.52 g as a mixture of starting material and 2-bromochloromethyl-1-chloro4-(difluoromethoxy)benzene ($R_f$ 0.51 (silica gel, CCl$_4$), and 3.84 g of the desired product ($R_f$ 0.42 (silica gel, CCl$_4$). The latter was crystallized from hexane: butyl chloride=9:1 at −50° C. to return 3.25 g (54%) of 2-bromomethyl-1-chloro4-(difluoromethoxy)benzene as a colorless oil.

Similarly prepared was: 3-bromomethyl-1-chloro-4-(difluoromethoxy)benzene as an oil in 56% yield.

Example 3

Preparation of 2-(2chloro-5-difluoromethoxy)phenyl)ethanenitrile

A solution/suspension of 1.07 g (21.8 mmol) of NaCN in 9 mL of dimethylformamide containing 255 µL of 6 N HCl was stirred with ice cooling as a solution of 4.25 g (15.7 mmol) of 2-bromomethyl-1-chloro-4-(difluoromethoxy)benzene in 6 mL of dimethylformamide was added dropwise over 5 minutes. The mixture was warmed to ambient temperature and stirred for 10 minutes, then diluted with 50 mL of water and extracted twice with butyl chloride. The extracts were filtered through 2 g of silica gel followed by 10 mL of solvent. Combined organics were stripped to an oil. Crystallization from butyl chloride at −50° C. gave in two crops 3.06 g (90%) of a white solid, m.p. 35-38° C.

Similarly prepared was: 2-(5chloro-2-(difluoromethoxy)phenyl)ethanenitrile as a white solid (78% yield.), m.p. 50.5-52 ° C. $R_f$ 0.40 (silica gel, butyl chloride).

Example 4

Preparation of 2-(2-chloro-5-difluoromethoxy)phenyl-3-hydroxypropanenitrile

A 25 mL flask with a stir bar was charged with 3.0 g (13.8 mmol) of2-(2-chloro-5-(difluoromethoxy)phenyl)ethanenitrile, 12 mL of ethanol and 1.34 mL of 37% formaldehyde solution. The mixture was stirred and a mixture of 115 µL of 40% Triton B in methanol and 38 µL of DBU was added. After a very mild exotherm, all solids dissolved. After 50 minutes at ambient temperature, the reaction was quenched by the addition of 0.5 mL of 3 N HCL. The mixture was filtered to remove floc, diluted with 2 volumes of water and extracted with butyl chloride. The extracts were water washed and stripped to an oil. This was chromatographed on 35 g of silica gel eluting with 5%→60% EtOAc in hexane to recover 2.2 g (65% yield.) of the desired product, $R_f$ 0.18 (silica gel, EtOAc:hexane=1:4).

Similarly prepared were:
2-(2,5-dichlorophenyl)-3-hydroxypropanenitrile as a white solid (52% yield.), m.p. 70.5-72.5° C.
2-(5-chloro-2-(difluoromethoxy)phenyl)-3-hydroxypropanenitrile as a white solid (73% yield.), as a colorless oil.
2-(2,4-dichlorophenyl)-3-hydroxypropanenitrile, as a white solid (48% yield.), m.p. 49.5-52° C. (crystallized from butyl chloride).

Example 5

Preparation of 3-acetoxy-2-(2-chloro-5-(difluoromethoxy)phenyl)propanenitrile (Ester 1)

A 5 mL screw-capped test tube was charged with 250 mg (1.00 mmol) of 2-(2-chloro-5-(difluoromethoxy)phenyl)-3-hydroxypropanenitrile, 0.4 mL of acetonitrile and 122 µL (1.3 mmol) of acetic anhydride. This mixture was stirred briefly with a melting point capillary having the tip wetted with conc. H$_2$SO$_4$ to give an immediate exotherm. After 15 minutes the mixture was diluted with water and extracted with butyl chloride. The extract was washed with water 3 times, dried (Na$_2$SO$_4$), and stripped of solvent under high vacuum to give 233 mg (96%) of the desired ester product, i.e., 3-acetoxy-2-(2-chloro-5-(difluoromethoxy)phenyl)propanenitrile, as a colorless oil.

Example 6

Preparation of 3-acetoxy-2-(2,5-dichlorophenyl)propanenitrile (Ester 2)

This ester was prepared using the procedure described in Example 5, except 2-(2,5-dichlorophenyl)-3-hydroxypropanenitrile was used in place of 2-(2-chloro-5-(difluoromethoxy)phenyl)-3-hydroxypropanenitrile. The preparation of 2-2,5-dichlorophenyl)-3-hydroxypropanenitrile is described in Example 4. The recovered ester product was a white solid (92% yield), m.p. 79-80.5° C.

Example 7

Preparation of 3-acetoxy-2-(5-chloro-2-(difluoromethoxy)phenyl)propanenitrile (Ester 3)

This ester was prepared using the procedure described in Example 5, except 2-(5-chloro-2-(difluoromethoxy)phenyl)-3-hydroxypropanenitrile was used in place of 2-(2-chloro-5-(difluoromethoxy)phenyl)-3-hydroxypropanenitrile. The preparation of 2-5-chloro-2-(difluoromethoxy)phenyl)-3-hydroxypropanenitrile is described in Example 4. The recovered ester product was a colorless oil.

Example 8

Preparation of 3-acetoxy-2-(2,4-dichlorophenyl)propanenitrile (Ester 4)

This ester was prepared using the procedure described in Example 5, except 2-(2,4-dichlorophenyl)-3-hydroxypropanenitrile was used in place of 2-(2-chloro-5-(difluoromethoxy)phenyl)-3-hydroxypropanenitrile. The preparation of 2-(2,4-dichlorophenyl)-3-hydroxypropanenitrile is described in Example 4. The recovered ester product was a white solid (77% yield), m.p. 48.5-50° C.

Example 9

Preparation of 2-2-(trifluoromethyl)phenyl)-3-hydroxypropanenitrile

A 50 µL (0.33 mmol) sample of DBU was injected into a stirred solution of 2-(2-(trifluoromethyl)phenyl)ethanenitrile (0.995 g, 4.86 mmol) and formaldehyde (600 µL of 30%) in THF (3 mL), producing a mild exotherm. After 45 min, the mixture was acidified (3N HCl), diluted with water and extracted with ethyl acetate. The organic phase was water washed, dried (MgSO$_4$) and stripped. The resulting colorless oil was flash chromatographed on silica gel (22 g) eluting with CH$_2$Cl$_2$→40% ethyl acetate/CH$_2$Cl$_2$. Fractions containing only product (R$_f$ 0.5 (silica gel, EtOAc:hexane=1:4)) were stripped to give 1.08 g (94% yield) of the desired alcohol.

Example 10

Preparation of 3-acetoxy-2-(2-(trifluoromethyl)phenyl)propanenitrile (Ester 5)

This ester was prepared using the procedure described in Example 5, except 2-(2-(trifluoromethyl)phenyl)-3-hydroxypropanenitrile was used in place of 2-(2-chloro-5-(difluoromethoxy)phenyl)-3-hydroxypropanenitrile. The preparation of 2-(2-(trifluoromethyl)phenyl)-3-hydroxypropanenitrile is described in Example 9. The recovered ester product was a colorless oil (95% yield), R$_f$ 0.35 (silica gel, ethyl acetate:hexane=1:4).

Example 11

Preparation of 2-(4-chloro-2-methylphenyl)-3-hydroxypropanenitrile

A sample of 4-chloro-2-methylbenzoic acid was converted to the ethyl ester using ethanol/triethyl orthoformate/sulfuric acid in >95% yield. Reduction of the ester with LiAiH$_4$/tetrahydrofuran gave 4-chloro-2-methylbenzyl alcohol in 97% yield as a colorless oil. Subsequent treatment with thionyl chloride/pyridine/CH$_2$Cl$_2$ gave the substituted benzyl chloride. The latter, on treatment with 40% excess sodium cyanide in DMF at 90° C. for 20 min. and normal work-up and crystallization from hexane/butyl chloride (2 crops) gave 4-chloro-2-methylbenzyl cyanide in 80% overall yield.

This latter compound on treatment with formaldehyde in the presence of DBU was found to quickly form an equilibrium at relatively low conversion to the desired alcohol which was then slowly dehydrated to an atroponitrile. Consequently, a mixture of the nitrile (688 mg, 4.15 mmol) and formaldehyde in THF (2.75 mL) was treated with DBU (55 µL), then quenched at 7 min with 3N HCl. Work-up recovered starting material (528 mg) by crystallization from butyl chloride/hexane. Two cycles of retreatment followed by flash chromatography (5%→90% ethyl acetate in hexane) recovered 313 mg of the desired alcohol as a pale yellow oil. TLC: R$_f$ 0.13 (silica gel, ethyl acetate:hexane=1:4).

Example 12

Preparation of 3-acetoxy-2-(4-chloro-2-methylphenyl)propanenitrile (Ester 6)

This ester was prepared using the procedure described in Example 5, except 2(-2-(4-chloro-2-methylphenyl)-3-hydroxypropanenitrile was used in place of 2-(2-chloro-5-(difluoromethoxy)phenyl-3-hydroxypropanenitrile. The preparation of 2(2-(4-chloro-2-methylphenyl)-3-hydroxypropanenitrile is described in Example 11. The recovered ester product was a white solid (74% yield in two crops), m. p. 61-63° C.

Example 13

Preparation of 2-(2-chlorophenyl)-3-hydroxypropanenitrile

A 330 µL sample of tetramethylammonium hydroxide (40% in water) was added with stirring to a solution of 750 mg (4.95 mmol) of 2-chlorophenylacetonitrile and 1.86 mL of 37% formaldehyde in 9 mL of tetrahydrofuran. The reaction was quenched at 12 min by acidification with 3 N HCl and diluted with ethyl acetate and water. The organic phase was washed with water, saturated salt solution, then stripped to an oil. This was flash chromatographed on 15 g of silica gel eluting with 5→90% ethanol in hexane. Fractions containing product were stripped to yield 622 mg (69%) of the alcohol as a colorless oil, R$_f$ 0.14 (silica gel, ethyl acetate:hexane=1:4).

Example 14

Preparation of 3-acetoxy-2-(2-chlorophenyl)propanenitrile (Ester 7)

This ester was prepared using the procedure described in Example 5, except 2-(2-chlorophenyl)-3-hydroxypropanenitrile was used in place of 2-2-chloro-5-(difluoromethoxy)phenyl-3-hydroxypropanenitrile. The preparation of 2-(2-chlorophenyl)-3-hydroxypropanenitrile is described in Example 13. The recovered ester product was a colorless oil (70% yield), R$_f$ 0.3 (silica gel, ethyl acetate:hexane=1:4).

Example 15

Preparation of 3-hydroxy-2-(4-chlorophenyl)propanenitrile

About 20% of a solution of p-chlorobenzyl cyanide (0.75 g, 4.94 mmol) and diethyl oxalate (0.87 mL, 6.4 mmol) in tetrahydrofuran (one mL) was added to a stirred suspension of sodium hydride (167 mg, 6.95 mmol) in tetrahydrofuran (4 mL). The mixture was heated at 35-40° C. until H$_2$ evolution began. The remaining mixture was added dropwise over about ten minutes. After H$_2$ evolution ceased, part of the solvent was removed under reduced pressure. The residue was diluted with 10 mL of water, neutralized with dilute sulfuric acid and extracted twice with ethyl acetate. The extract was water washed, dried (MgSO$_4$) and stripped to a light brown solid. This was triturated with hexane, filtered and dried to give 1.17 g, (94%yield) of ethyl 3-(4-chlorophenyl)-3-cyano-2-oxopropanoate.

Sodium carbonate (204 mg, 1.9 mmol) dissolved in water (1.2 mL) was added dropwise over 10,min to a vigorously stirred mixture of the above ethyl 3-(4-chlorophenyl)-3-cyano-2-oxopropanoate (400 mg 1.59 mmol), 37% HCHO (131 µL 1.75 mmol) and methylene chloride (2 mL). After an additional 2 min, the mixture was diluted with ~one mL each of water and methylene chloride and phase separated. Acidification of the aqueous phase and filtration of the precipitated solid recovered 68 mg (17%) of the starting material. The organic phase was washed twice with water, dried and stripped to give a colorless oil. Flash chromatography on 10 g of silica gel eluting with 5→50% ethyl acetate in hexane recovered 43 mg of a higher R$_f$ product assumed to be 4-chloroatroponitrile, and 210 mg (75%) of the desired alcohol, R$_f$ 0.09 (silica gel, ethyl acetate:hexane=1:4).

Example 16

Preparation of 3-acetoxy-2-(4chlorophenyl)propanenitrile (Ester 8)

This ester was prepared using the procedure described in Example 5, except 3-hydroxy-2-4-chlorophenyl)propanenitrile was used in place of 2-2-chloro-5-difluoromethoxy)phenyl)-3-hydroxypropanenitrile. The preparation of 3-hydroxy-2-(4-chlorophenyl)propanenitrile is described in Example 15. The recovered ester product was a colorless oil (79% yield).

Example 17

Preparation of 2-(4-methoxyphenyl)-3-hydroxybutanenitrile

One third of a solution of p-methoxybenzylcyanide (1.0 g, 6.75 mmol) and ethyl acetate (1 mL, ~10 mmol) in tetrahydrofuran (3 mL) was added to a stirred suspension of sodium hydride (540 mg of 60% in mineral oil, 13.5 mmol) in tetrahydrofuran (3 mL). After 10 minutes, $H_2$ evolution became moderate. After 30 minutes, an additional third of the mixture was added, and the remainder added after an additional 15 minutes. The mixture was heated at 50-55° C. for 20 minutes and cooled. The mixture was extracted with chloroform to remove mineral oil, acidified with dilute HCl and twice extracted with chloroform. Organic extracts were dried ($MgSO_4$) and stripped to 1.24 g of pale yellow solid. Trituration with 20% chloroform in hexane and filtration recovered 1.14 g (89% yield) of white solid, 2-(4-methoxy phenyl)-3-oxobutanenitrile, m. p. 81-82° C.

Sodium cyanoborohydride (134 mg, 2.13 mmol) was added all at once to a stirred mixture of the above 2-(4-methoxyphenyl)-3-oxobutanenitrile (200 mg, 1.05 mmol), ethanol (1.25 mL) and glacial acetic acid (70 μL). Stir and heat at 70-75° C. for 1.75 hr. Dilute cooled mixture with three volumes of water, extract three times with ethyl acetate, wash combined extracts with water, saturated NaCl solution, dry and strip to give 241 mg of oil. This was chromatographed on 6 g of silica gel eluting with 5-30% acetone in hexane. Combined product fractions were stripped to yield 193 mg (95% yield) oil, 2-4-methoxyphenyl-3-hydroxy butanenitrile, as a mixture of diasteromers.

Using ethyl acetate, ethyl formate or ethyl methoxyacetate for the preparation of the appropriate oxo-intermediates followed by reduction with sodium cyanoborohydride as above, the following were similarly prepared:

2-(4-chlorophenyl)-3-hydroxybutanenitrile, a slightly yellow oil as a mixture of diastereoisomers (92.5% yield), $R_f$ 0.60 (silica gel, acetone:hexane=1:1).

2-(4-chlorophenyl)-3-hydroxy-4-methoxybutanenitrile, an oil as a mixture of diastereoisomers (88% yield).

2-(4-methylphenyl)-3-hydroxypropanenitrile, pale yellow oil (98% yield).

2-(4-methylphenyl)-3-hydroxybutanenitrile, pale yellow oil as a mixture of diastereoisomers (99% yield).

2-(4-methylphenyl)-3-hydroxy-4-methoxybutanenitrile, yellow oil as a mixture of diastereoisomers (95% yield).

2-(4-methoxyphenyl)-3-hydroxypropanenitrile, pale yellow oil (99% yield).

2-(4-methoxyphenyl)-3hydroxybutanenitrile, an oil as a mixture of diastereoisomers (95% yield).

3-hydroxy-2-phenylbutanenitrile, an oil as a mixture of diastereoisomers (95% yield).

Example 18

Preparation of 3-acetoxy-2-phenylbutanenitrile (Ester 9)

This mixture of esters was prepared using the procedure described in Example 5, except 3-hydroxy-2-phenylbutanenitrile was used in place of 2-(2-chloro-5-difluoromethoxy)phenyl)-3-hydroxypropanenitrile. The preparation of 3-hydroxy-2-phenylbutanenitrile is shown in Example 17. The recovered ester product was a colorless oil (93% yield) as a mixture of diastereoisomers (Esters 9A and 9B), separated by chromatography into two pairs, $R_f$ 0.40 and 0.32 (silica gel, EtOAc:hexane=1:4).

Example 19

Preparation of 3-acetoxy-2-(4-chlorophenyl)butanenitrile (Ester 10)

This ester was prepared using the procedure described in Example 5, except 2-(4-chlorophenyl)-3-hydroxybutanenitrile was used in place of 2-(2-chloro-5-(difluoromethoxy)phenyl)-3-hydroxypropanenitrile. The preparation of 2-(4-chlorophenyl)-3-hydroxybutanenitrile is described in Example 17. The recovered ester product was a mixture of diastereoisomers (85% yield), $R_f$ 0.29 and 0.35 (silica gel, acetone:hexane=1:3).

Example 20

Preparation of 3-acetoxy-2-(4-chlorophenyl)-4-methoxybutanenitrile (Ester 11)

This ester was prepared using the procedure described in Example 5, except 2-(4-chlorophenyl)-3-hydroxy-4-methoxybutanenitrile was used in place of 2-(2-chloro-5-(difluoromethoxy)phenyl)-3-hydroxypropanenitrile. The preparation of 2-(4-chlorophenyl)-3-hydroxy-4-methoxybutanenitrile is described in Example 17. The recovered ester product was a yellow oil (67% yield).

Example 21

Preparation of 3-acetoxy-2-(4-methylphenyl)propanenitrile (Ester 12)

This ester was prepared using the procedure described in Example 5, except 2-(4-methylphenyl)-3-hydroxypropanenitrile was used in place of 2-(2-chloro-5-(difluoromethoxy)phenyl)-3-hydroxypropanenitrile. The preparation of 2-(4-methylphenyl)-3-hydroxypropanenitrile is described in Example 17. The recovered ester product was a colorless oil (94% yield).

Example 22

Preparation of 3-acetoxy-2-(4-methylphenyl)butanenitrile (Ester 13)

This ester was prepared using the procedure described in Example 5, except 2-(4-methylphenyl)-3-hydroxybutanenitrile in place of 2-2-chloro-5-(difluoromethoxy)phenyl)-3-hydroxypropanenitrile in the above described procedure. The preparation of 2-(4-methylphenyl)-3-hydroxybutanenitrile is described in Example 17. The recovered ester product was a colorless oil (85% yield).

Example 23

Preparation of 3-acetoxy-2-(4-methylphenyl)-4methoxybutanenitride (Ester 14)

This ester was prepared using the procedure described in Example 5, except 2-(4-methylphenyl)-3-hydroxy-4-methoxybutanenitrile was used in place of 2-(2-chloro-5-(difluoromethoxy)phenyl)-3-hydroxypropanenitrile. The preparation of 2-(4methylphenyl)-3-hydroxy-4-methoxybutanenitrile is described in Example 17. The recovered ester product was a yellow oil (86% yield.).

Example 24

Preparation of 3-acetoxy-2-(4-methoxyphenyl)propanenitrile (Ester 15)

This ester was prepared using the procedure described in Example 5, except 2-(4-methoxyphenyl)-3-hydroxypropanenitrile was used in place of 2-(2-chloro-5-(difluoromethoxy)phenyl)-3-hydroxypropanenitrile. The preparation of 2-(4-methoxyphenyl)-3-hydroxypropanenitrile is described in Example 17. The recovered ester product was a pale yellow oil (87% yield).

Example 25

Preparation of 3-acetoxy-2-(4-methoxyphenyl)butanentrile (Ester 16)

This ester was prepared using the procedure described in Example 5, except 2-(4-methoxyphenyl)-3-hydroxybutanenitrile was used in place of 2-(2-chloro-5-(difluoromethoxy)phenyl)-3-hydroxypropanenitrile. The preparation of 2-(4-methoxyphenyl)-3-hydroxybutanenitrile is described in Example 17. The recovered ester product was a viscous colorless oil (85% yield).

Example 26

Preparation of 3-acetoxy-2-(4-methoxyphenyl)-4-methoxybutanenitrile (Ester 17)

This ester was prepared using the procedure described in Example 5, except 2-(4-methoxyphenyl)-3-hydroxy-4-methoxybutanenitrile was used in place of 2-(2-chloro-5-(difluoromethoxy)phenyl)-3-hydroxypropanenitrile. The preparation of 2-(4-methoxyphenyl)-3-hydroxy-4-methoxybutanenitrile is described in Example 17. The recovered ester product was a yellow oil (72% yield).

Example 27

Preparation of ethyl 3-(4-chlorophenyl)-2-hydroxy-3-cyanopropanoate

A 542 µL (3.63 mmol) sample of DBU was added to a solution of 500 mg (3.30 mmol) of 4-chlorophenylacetonitrile and 493 µL (3.63 mmol) of diethyloxalate in 1.6 mL of acetonitrile. After ca. 10 min, the mixture was diluted with ethyl acetate and acidified with dilute HCl. The organic phase was washed with three portions of water, dried and stripped to an oily solid. Trituration with hexane/butyl chloride yielded 414 mg, m. p. 135-136° C. A second crop of 35 mg gave a total yield of 54% of ethyl 3-(4-chlorophenyl)-3-cyano-2-oxopropanoate.

Sodium cyanoborohydride (52 mg. 0.827 mmol) was added all at once to a stirred solution of the above compound (150 mg. 0.596 mmol) in ethanol (one mL) and acetic acid (40 µL). The mixture was stirred at 70° C. for one hour, cooled, diluted with 4 mL of water, extracted with ethyl acetate, and the extract was washed with water, dried (MgSO$_4$), and stripped to an oil. Flash chromatography on silica gel (hexane/acetone) gave the pure title compound, 128 mg (85%).

Example 28

Preparation of ethyl 2-acetoxy-3-(4-chlorophenyl)-3-cyanopropanoate (Ester 18)

This ester was prepared using the procedure described in Example 5, except ethyl 3-(4-chlorophenyl)-2-hydroxy-3-cyanopropanoate was used in place of 2-(2-chloro-5-(difluoromethoxy)phenyl)-3-hydroxypropanenitrile. The preparation of ethyl 3-(4-chlorophenyl)-2-hydroxy-3-cyanopropanoate is described in Example 27. The recovered ester product was a viscous oil (86% yield).

Example 29

Preparation of 2-(2-chloro-5-(difluoromethoxy)phenyl)-3-(formyloxy)propanenitrile (Ester 19)

A 5 mL test tube with septum/screw-cap and stir bar was charged with 0.75 mL of acetonitrile and 39 µL (0.50 mmol) of dimethylformamide. The mixture was stirred and ice cooled, and with cap loosened, 42 µL (0.48 mmol) of oxalyl chloride was added giving gas evolution and formation of solid Vilsmeier Reagent. A 100 mg (0.40 mmol) sample of 2-(2-chloro-5-(difluoromethoxy)phenyl)-3-hydroxypropanenitrile (as prepared in Example 4) in 0.25 mL of acetonitrile was added. The resulting solution was poured into 1 mL of N HCL and extracted with butyl chloride. The organic phase was water washed and stripped of most solvent, then chromatographed on 5 g of silica gel eluting with 5% →40% EtOAc in hexane to recover 97 mg (87% yield) of the desired formate ester, i.e., 2-(2-chloro-5-(difluoromethoxy)phenyl)-3-(formyloxy)propanenitrile, as a colorless oil.

Example 30

Preparation of 2-(2,5-dichlorophenyl)-3-(formyloxy)propanenitrile (Ester 20)

This ester was prepared using the procedure described in Example 29, except 2-(2,5-dichlorophenyl)-3-hydroxypropanenitrile was used in place of 2-2-chloro-5-(difluoromethoxy)phenyl)-3-hydroxypropanenitrile. The recovered ester product was a white solid (from butyl chloride, 48% yield), m. p. 90.5-92.5° C.

Example 31

Preparation of 2-(2-chloro-5-(difluoromethoxy)phenyl)-3-phenylacetoxy)propanenitrile (Ester 21)

The anhydride of phenylacetic acid was prepared as follows: A 0.5 g (3.67 mmol) sample of the acid and 1 µL of dimethylformamide was treated with 2.75 mL of 2 M thionyl chloride in $CH_2Cl_2$. The mixture was protected from moisture and heated at 40° C. for 1.5 hours. Solvent and excess $SOCl_2$ were stripped under vacuum, then 3 mL of butyl chloride was added and stripped. The resulting oil was dissolved in 2 mL of butyl chloride and 0.5 g of additional phenylacetic acid was added. This mixture was stirred with ice cooling as 0.37 mL (3.7 mmol) of pyridine in 2 mL of butyl chloride was added to give a precipitate of white gum. After 10 minutes, 3 mL of EtOAc was added and stirred. The resulting liquid phase was separated, stripped to a clear oil which was diluted to 2 mL with acetonitrile. A 0.55 mL aliquot of this solution was treated with 200 mg (0.888 mmol) of 2-(2-chloro-5-difluoromethoxy)phenyl)-3-hydroxypropanenitrile and 2.5 µL of conc. $H_2SO_4$. The mixture was heated at 75° C. for 30 minutes, cooled, diluted with water, and extracted with butyl chloride. Stripping the extracts gave an oil which was chromatographed on 10 g of silica gel eluting with 50%→100% butyl chloride in hexane. Stripping product fractions gave 150 mg (46% yield) of the desired ester, i.e., 2-(2-chloro-5-(difluoromethoxy)phenyl)-3-(phenylacetoxy)propanenitrile, as an oil. $R_f$ 0.43 (silica gel, EtOAc:hexane=1:4).

Example 32

Preparation of 3-acetoxy-2-phenylpropanenitrile (Ester 22)

3-Oxo-2-phenylpropanenitrile was prepared by addition of a mixture of phenylacetonitrile (0.90 g, 7.68 mmol) and ethyl formate (0.85 g, 11.5 mmol) dropwise to a stirred suspension of sodium hydride (0.41 g of 60%, 10 mmol) in tetrahydrofuran (4.5 mL). Reaction was rapid and exothermic. After heating in an oil bath at 50° C. for 20 min., the mixture was carefully acidified with dilute HCl and extracted with ethyl acetate. Extracts were washed with water, saturated NaCl solution, dried ($MgSO_4$) and stripped to give 0.96 g (86%) of off-white solid, m. p. 148-153° C., $R_f$ 0.5 (silica gel, ethanol:ethyl acetate:hexane=1:4:4).

A portion of the above product (435 mg, 3.0 mmol) was reduced by addition to a stirred solution of sodium cyanoborohydride (300 mg) and acetic acid (200 µL) in tetrahydrofuran (3.5 mL). Stir and heat at 70° C. for 20 min., cool, partially strip, dilute with water and extract with ethyl acetate (4×). Extracts were washed with water, saturated NaCl solution and stripped. Flash chromatography recovered 137 mg of 2-phenyl-3-hydroxypropanenitrile. An additional 279 mg of less pure product was also obtained.

A sample of this 2-phenyl-3-hydroxypropanenitrile (127 mg, 0.863 mmol) and acetic anhydride (106 µL, 1.1 mmol) in acetonitrile (250 µL) was treated with sulfuric acid (~0.5 µL). After 25 min at ambient temperature, work-up as described above in Example 5 gave 160 mg (98%) product as a colorless oil.

Example 33

Preparation of 3-acetoxy-2-3-phenoxyphenyl)propanenitrile (Ester 23)

3-Oxo-2-(3-phenoxyphenyl)propanenitrile was prepared on a 2.39 mmol scale from 3-phenoxyphenylethanenitrile and ethyl formate using the procedure described for the preparation of 2-(4-methoxyphenyl)-3-oxobutanenitrile in Example 17. The product was a viscous orange oil (84% yield).

A 175 mg (0.738 mmol) sample of the above 3-oxo-2-3-phenoxyphenyl)propanenitrile was reduced using sodium cyanoborohydride (51 mg, 0.81 mmol) in ethanol (1.25 mL) and acetic acid (90 µL) using the procedure described in Example 17 to give 158 mg (89% yield) of 3-hydroxy-2-(3-phenoxyphenyl)propanenitrile as a pale yellow viscous oil.

A 175 mg (0.738 mmol) sample of the above 3-hydroxy-2-(3-phenoxyphenyl)propanenitrile was acylated with acetic anhydride (74 µL) in acetonitrile (300 µL) using the procedure described in Example 5 to give 147 mg (86% yield) of 3-acetoxy-2-(3-phenoxyphenyl)propanenitrile as a colorless oil.

Example 34

Preparation of 3-acetoxy-2-(4-chlorophenyl)-3-methylbutanenitrile (Ester 24)

A mixture of 4-chlorophenyacetonitrile (1 gr. 5.37 mmol), DBU (14 mg) and acetone (2 mL) was warmed to reflux for ~6-7 minutes, cooled, and diluted with 3 mL of butyl chloride. The solution was treated with 3 drops of 3N HCl, washed with water and saturated NaCl solution and the organic layer was filtered through a small pad of anhydrous magnesium sulfate. The resulting solution was chilled to −50° C. and seeded with the starting nitrile. After crystallization was complete, the supernatant liquid was withdrawn. The resulting wet solid was allowed to partially melt, then re cooled and again the supernatant liquid was withdrawn The solid was allowed to melt and stripped of solvent to return 0.75 g starting nitrile which was retreated with acetone and DBU, reacted and worked up as above. The combined supernatant was stripped to an oil. This was dissolved in one mL of acetonitrile, treated with 0.3 mL of acetic anhydride, then stirred with a m.p. tube with tip wetted with conc. $H_2SO_4$ to give a slow exotherm to ~35° C. This was heated briefly to ~80° C., cooled, and 0.5 mL of ethanol added to remove excess acetic anhydride. The mixture was diluted with 3 mL of ethyl acetate, washed with water, dried ($MgSO_4$) and stripped to an oil. The oil was purified by radial chromatography using butyl chloride followed by a hexane-ethyl acetate gradient. Stripping pure fractions returned 110 mg. $R_f$ 0.4 (silica gel, EtOAc/hexane=¼) of the desired ester.

Example 35

Fungicidal Activity of Various Esters of the Invention

To demonstrate the fungicidal activity of the esters of the invention, a number of esters in accordance with the invention were tested against various representative microorganisms to determine their fungistatic endpoint. The microorganisms involved in these tests were *Aspergillis niger, Candida albicans, Trichophyton metagrophytes,* and *Pichia pastoris*. The various esters tested are listed in the following table together with their fungistatic endpoints.

Fungistatic endpoints were determined by combining the compounds at several dosage levels in a culture medium which had been freshly inoculated with spores of the test organisms. Five mL aliquots were placed in sterile culture tubes. The test compounds dissolved in the appropriate solvent were added to obtain the desired concentration of the compound in the culture medium. Following incubation at suitable conditions, the presence of growth was determined visually at each concentration of the biocide. The lowest concentration of the compound preventing growth was taken as the fungistatic endpoint. Controls containing the solvent alone at the highest dosage were made to insure that no microbial inhibition was produced by the solvent.

The culture media used in these tests was the Bushnell-Haas medium from Difco. Dextrose at 10 g/L and yeast extract at 0.1 g/L were added to obtain growth of the test organisms. The dilute solution of the Bushnell Haas media which was used in these tests contains: 0.20 g/L magnesium sulfate; 0.02 g/L calcium chloride; 1.00 g/L monopotassium phosphate; 1.00 g/L dipotassium phosphate; 1.00 g/L ammonium nitrate, and 0.05 g/L ferric chloride. The final pH of the media was 7.0±0.2 at 25° C.

| Fungistatic Endpoint (ppm Range) | | | | |
|---|---|---|---|---|
| Ester Tested | Test Organism | | | |
| Example No. | *T. metagrophytes* | *Aspergillis niger* | *Candida albicans* | *Pichia. pastoris* | Comments |
| 5 | <16 | — | <16 | — | |
| 6 | <16 | — | <16 | — | |
| 7 | 32 | — | 32 | 32 | |
| 8 | 16-32 | — | 16 | <16 | |
| 10 | >64 | 128-256 | >64 | >64 | |
| 12 | >64 | 64-128 | >64 | >64 | |
| 14 | 32 | — | 16 | 16 | |
| 16 | <16 | — | <16 | <16 | |
| 18 | >64 | 256-512 | >64 | >64 | Isomer pair 1 |
| 18 | >64 | 128 | >64 | >64 | Isomer pair 2 |
| 19 | 32-64 | — | 16-32 | 16 | Isomer mix |
| 20 | — | 64-128 | — | — | Isomer mix |
| 21 | — | 64 | — | — | |
| 22 | — | 128-256 | — | — | Isomer mix |
| 23 | — | 128-256 | — | — | Isomer mix |
| 24 | — | 128 | — | — | |
| 25 | — | 128-256 | — | — | Isomer mix |
| 26 | — | 128-256 | — | — | Isomer mix |
| 28 | — | 128 | — | — | Isomer mix |
| 29 | <16 | <16 | <16 | — | |
| 30 | <16 | <16 | <16 | — | |
| 31 | <16 | — | >64 | 64 | |
| 32 | 16 | — | >64 | 16-32 | |
| 33 | — | 128-256 | — | — | |

The results of these tests indicate that the esters in accordance with the invention are effective in controlling the growth of a variety of microorganisms, including human-pathogenic fungi, at very low concentrations, i.e., at concentrations of less than 256 ppm (0.0256%), and in some cases at concentrations less than 32 ppm (0.0032%) and in a number of cases at concentrations less than 16 ppm (0.0016%). Because of their outstanding activity, the esters of the invention have potential utility in a wide range of applications, especially therapeutic uses such as the treatment of ring worm and athlete's foot, as well as fungal infection of the toenails (onychomycosis).

While certain representative embodiments and details have been shown in the foregoing examples for the purpose of illustrating the invention, it will be apparent to those skilled in the art that various changes and modifications can be made therein without departing from the scope of the invention.

I claim as my invention:

1. An ester of a phenylalkanenitrile having the formula:

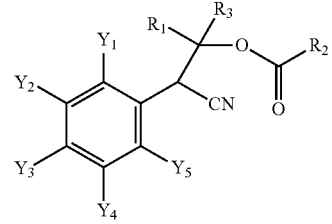

wherein $R_1$ is hydrogen, $C_1$-$C_5$ alkyl, $C_1$-$C_5$ alkoxyalkyl, or $C_1$-$C_5$ alkoxycarbonyl, $R_2$ is hydrogen, $C_1$-$C_5$ alkyl, phenyl or $CH_2$-phenyl, $R_3$ is hydrogen, $C_1$-$C_5$ alkyl, and $Y_1$, $Y_2$, $Y_3$, $Y_4$ and $Y_5$ are individually or collectively hydrogen, halogen, methyl, —$CHF_2$, —$CF_3$, —$OCHF_2$, —$OCF_3$, $C_1$-$C_5$ alkoxy, phenoxy, or —$SF_5$, with the proviso that at least two of $Y_1$, $Y_2$, $Y_3$, $Y_4$ and $Y_5$ must be hydrogen.

2. The ester of claim 1 wherein $R_1$ is hydrogen, methyl, methoxy methyl, $R_2$ is hydrogen, $C_1$-$C_5$ alkyl, phenyl or $CH_2$-phenyl, $R_3$ is hydrogen or methyl, $Y_1$ is hydrogen, halogen, methyl, trifluoromethyl or difluoromethoxy, $Y_3$ is hydrogen, halogen, methyl or methoxy, and $Y_2$, $Y_4$ and $Y_5$ are hydrogen.

3. The ester of claim 1 wherein $R_1$ is hydrogen or methyl, $R_2$ is hydrogen, $C_1$-$C_5$ alkyl, phenyl or $CH_2$-phenyl, $R_3$ is hydrogen or methyl, $Y_1$ is hydrogen, halogen or difluoromethoxy, $Y_4$ is hydrogen, halogen or difluoromethoxy, and $Y_2$, $Y_3$ and $Y_5$ are hydrogen.

4. The ester of claim 2 wherein $R_1$ is hydrogen or methyl, and $R_2$ is hydrogen or methyl, $R_3$ is hydrogen, and $Y_1$ and $Y_3$ are hydrogen, chlorine or difluoromethoxy.

5. The ester of claim 3 wherein $R_1$ is hydrogen or methyl, and $R_2$ is hydrogen or methyl, $R_3$ is hydrogen, and $Y_1$ and $Y_4$ are hydrogen, chlorine, trifluoromethyl or difluoromethoxy.

6. The ester of claim 1 wherein $R_1$ is hydrogen, $R_2$ is methyl, $R_3$ is hydrogen, $Y_1$ is chlorine, trifluoromethyl or difluoromethoxy, $Y_4$ is hydrogen, chlorine or difluoromethoxy, and $Y_2$, $Y_3$ and $Y_5$ are hydrogen.

7. The ester of claim 1 wherein $R_1$ is hydrogen, $R_2$ is hydrogen or $CH_2$-phenyl, $R_3$ is hydrogen, $Y_1$ is chlorine, $Y_4$ is chlorine or difluoromethoxy, and $Y_2$, $Y_3$ and $Y_5$ are hydrogen.

8. The ester of claim 1 wherein $R_1$ is hydrogen or methyl, $R_2$ is methyl, $R_3$ is hydrogen, $Y_1$ and $Y_3$ are hydrogen, chlorine or methoxy, and $Y_2$, $Y_4$ and $Y_5$ are hydrogen.

9. A fungicidal composition for combating the growth of fungi comprising a liquid or solid carrier and an effective antifungal amount of an ester of a phenylalkanenitrile having the formula:

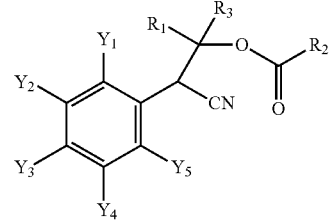

wherein $R_1$ is hydrogen, $C_1$-$C_5$ alkyl, $C_1$-$C_5$ alkoxyalkyl, $C_1$-$C_5$ alkoxy methyl, or $C_1$-$C_5$ alkoxycarbonyl, $R_2$ is hydrogen, $C_1$-$C_5$ alkyl, phenyl or $CH_2$-phenyl, $R_3$ is hydrogen, $C_1$-$C_5$ alkyl, or substituted phenyl, and $Y_1$, $Y_2$, $Y_3$, $Y_4$ and $Y_5$ are individually or collectively hydrogen, halogen, methyl, —$CHF_2$, —$CF_3$, —$OCHF_2$, —$OCF_3$, $C_1$-$C_5$ alkoxy, phenoxy, or —$SF_5$, with the proviso that at least two of $Y_1$, $Y_2$, $Y_3$, $Y_4$ and $Y_5$ must be hydrogen.

10. The fungicidal composition of claim 9 wherein $R_1$ is hydrogen, methyl, methoxy methyl, $R_2$ is hydrogen, $C_1$-$C_5$ alkyl, phenyl or $CH_2$-phenyl, $R_3$ is hydrogen or methyl, $Y_1$ is hydrogen, halogen, methyl, trifluoromethyl or difluoromethoxy, $Y_3$ is hydrogen, halogen, methyl or methoxy, and $Y_2$, $Y_4$ and $Y_5$ are hydrogen.

11. The fungicidal composition of claim 9 wherein $R_1$ is hydrogen or methyl, $R_2$ is hydrogen, $C_1$-$C_5$ alkyl, phenyl or $CH_2$-phenyl, $R_3$ is hydrogen or methyl, $Y_1$ is hydrogen, halogen or difluoromethoxy, $Y_4$ is hydrogen, halogen or difluoromethoxy, and $Y_2$, $Y_3$ and $Y_5$ are hydrogen.

12. A method of inhibiting the growth of fungi comprising contacting the fungi with a growth inhibiting amount of a phenylalkanenitrile having the formula:

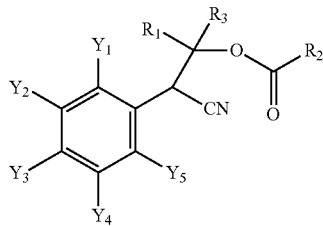

wherein $R_1$ is hydrogen, $C_1$-$C_5$ alkyl, $C_1$-$C_5$ alkoxyalkyl, $C_1$-$C_5$ alkoxy methyl, or $C_1$-$C_5$ alkoxycarbonyl, $R_2$ is hydrogen, $C_1$-$C_5$ alkyl, phenyl or $CH_2$-phenyl, $R_3$ is hydrogen, $C_1$-$C_5$ alkyl, or substituted phenyl, and $Y_1$, $Y_2$, $Y_3$, $Y_4$ and $Y_5$ are individually or collectively hydrogen, halogen, methyl, —$CHF_2$, —$CF_3$, —$OCHF_2$, —$OCF_3$, $C_1$-$C_5$ alkoxy, phenoxy, or —$SF_5$, with the proviso that at least two of $Y_1$, $Y_2$, $Y_3$, $Y_4$ and $Y_5$ must be hydrogen.

13. The method of claim 12, wherein the fungi are contacted with a growth-inhibiting amount of a phenylalkanenitrile having the specified formula wherein $R_1$ is hydrogen, methyl, methoxy methyl, $R_2$ is hydrogen, $C_1$-$C_5$ alkyl, phenyl or $CH_2$-phenyl, $R_3$ is hydrogen or methyl, $Y_1$ is hydrogen, halogen, methyl, trifluoromethyl or difluoromethoxy, $Y_3$ is hydrogen, halogen, methyl or methoxy, and $Y_2$, $Y_4$ and $Y_5$ are hydrogen.

14. The method of claim 12, wherein the fungi are contacted with a growth-inhibiting amount of a phenylalkanenitrile having the specified formula wherein $R_1$ is hydrogen or methyl, $R_2$ is hydrogen, $C_1$-$C_5$ alkyl, phenyl or $CH_2$-phenyl, $R_3$ is hydrogen or methyl, $Y_1$ is hydrogen, halogen or difluoromethoxy, $Y_4$ is hydrogen, halogen or difluoromethoxy, and $Y_2$, $Y_3$ and $Y_5$ are hydrogen.

* * * * *